United States Patent
Geisberger

(10) Patent No.: US 8,546,596 B2
(45) Date of Patent: Oct. 1, 2013

(54) HYDROSILYLATION METHOD

(75) Inventor: Gilbert Geisberger, Altoetting (DE)

(73) Assignee: Wacker Chemie AG, Munich (DE)

( * ) Notice: Subject to any disclaimer, the term of this patent is extended or adjusted under 35 U.S.C. 154(b) by 970 days.

(21) Appl. No.: 12/486,190

(22) Filed: Jun. 17, 2009

(65) Prior Publication Data

US 2009/0318724 A1 Dec. 24, 2009

(30) Foreign Application Priority Data

Jun. 20, 2008 (DE) .................. 10 2008 002 552

(51) Int. Cl.
*C07F 7/00* (2006.01)

(52) U.S. Cl.
USPC ....................................................... 556/443

(58) Field of Classification Search
USPC ....................................................... 556/443
See application file for complete search history.

(56) References Cited

U.S. PATENT DOCUMENTS

| | | | |
|---|---|---|---|
| 5,422,412 A * | 6/1995 | Morita et al. ................. 528/25 |
| 5,527,935 A * | 6/1996 | Stepp et al. .................. 556/445 |
| 5,919,883 A | 7/1999 | Dittrich et al. | |
| 7,396,894 B2 | 7/2008 | Geisberger et al. | |
| 2005/0239986 A1 | 10/2005 | Geisberger et al. | |
| 2006/0116525 A1 * | 6/2006 | Geisberger et al. ........... 556/466 |
| 2007/0078277 A1 * | 4/2007 | Ackermann ................. 556/470 |
| 2007/0290202 A1 * | 12/2007 | Matsumoto et al. ........... 257/40 |

FOREIGN PATENT DOCUMENTS

| | | |
|---|---|---|
| CN | 1690104 A | 11/2005 |
| JP | 2007246602 A | 9/2007 |

\* cited by examiner

*Primary Examiner* — Johann R Richter
*Assistant Examiner* — Kofi Adzamli
(74) *Attorney, Agent, or Firm* — Brooks Kushman P.C.

(57) ABSTRACT

Compounds containing carbon-carbon double bonds and/or carbon-carbon triple bonds are hydrosilylated with linear organopolysiloxanes having diorganosiloxy units and Si—H groups, produced by reacting diorganodichlorosilanes and monochlorosilanes and optionally dichlorosilanes with water in a first step, where at least one of the monochlorosilanes or dichlorosilanes contain Si—H groups to give a partial hydrolysate and gaseous hydrogen chloride, and in a second step, treating the partial hydrolysate with water to remove SiCl groups still present to form hydrochloric acid, and producing a hydrolysate containing the organopolysiloxanes.

3 Claims, 1 Drawing Sheet

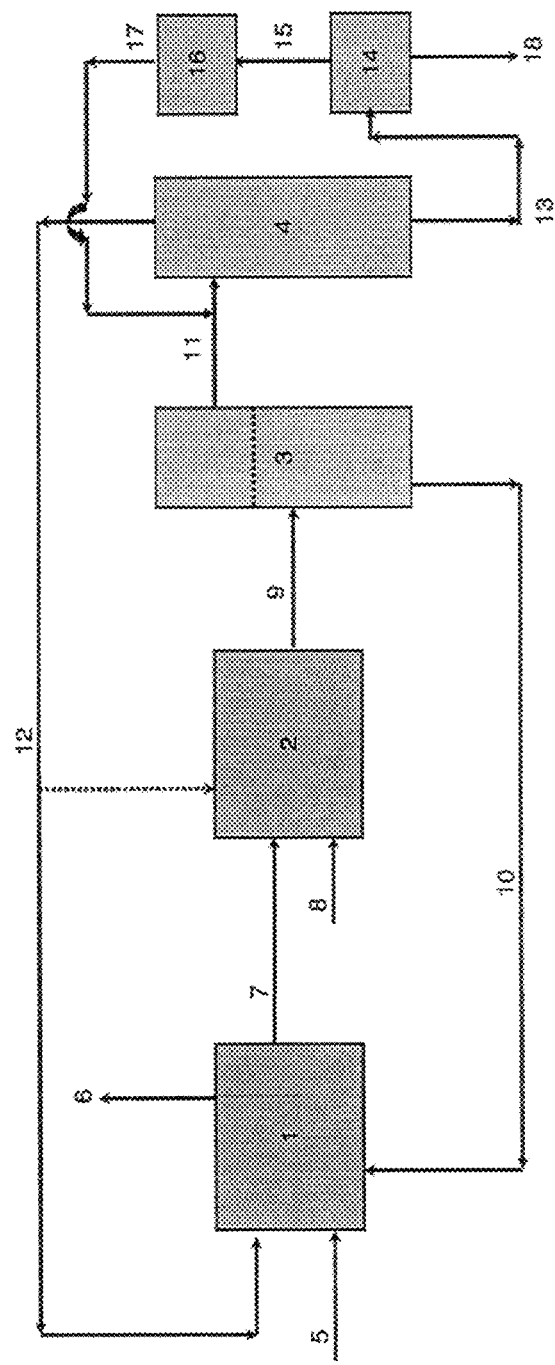

HYDROSILYLATION METHOD

BACKGROUND OF THE INVENTION

1. Field of the Invention

The invention relates to a method for the hydrosilylation of compounds (F) containing carbon-carbon double bonds and/or carbon-carbon triple bonds with linear organopolysiloxanes (Q) having diorganosiloxy units and Si—H groups, which are produced in a cohydrolysis method.

2. Background Art

The hydrosilylation of unsaturated compounds (F) with linear organopolysiloxanes (Q) having diorganosiloxy units and Si—H groups, which have hitherto been produced via equilibration methods (e.g. EP 797612) is prior art. A subsequent hydrosilylation with these "H equilibrates" requires a large amount of platinum catalyst, long reaction times, and/or high reaction temperatures. In addition, considerable product coloration occurs.

SUMMARY OF THE INVENTION

It is an object of the invention to improve upon the prior art, and in particular to provide a cost-effective method in which a lower concentration of platinum catalyst is required, less product coloration occurs and shorter reaction times or lower reaction temperatures are required. These and other objects are met by preparing a "non-equilibrate" Si—H-functional linear organopolysiloxane directly from the corresponding chlorosilanes, including at least one chlorosilane having Si—H functionality, in a two step process wherein a partial hydrolysis liberating gaseous hydrogen chloride is first conducted, and then full hydrolysis of remaining silicon-bonded chlorine is effected.

BRIEF DESCRIPTION OF THE DRAWINGS

FIG. 1 illustrates one embodiment of a continuous process used to prepare the Si—H-functional organopolysiloxanes used in the method of the invention.

DETAILED DESCRIPTION OF THE PREFERRED EMBODIMENT(S)

The invention thus provides a method for the hydrosilylation of compounds (F) containing carbon-carbon double bonds or carbon-carbon triple bonds with linear organopolysiloxanes (Q) having diorganosiloxy units and Si—H groups, which are produced by a process, wherein in a first step, diorganodichlorosilanes (A) and monochlorosilanes (B) and optionally dichlorosilanes (C), where at least the monochlorosilanes (B) or dichlorosilanes (C) contain Si—H groups, are reacted with water to give a partial hydrolysate (T) and gaseous hydrogen chloride and, in a second step, the partial hydrolysate (T) is treated, in order to remove the SiCl groups still present, with water to form hydrochloric acid, producing a hydrolysate (H) containing the organopolysiloxanes (Q).

In the inventive method, the organopolysiloxanes (Q) are produced directly from the chlorosilanes. The additional stage which has hitherto been required, the equilibration of at least two different organopolysiloxanes, is dispensed with. The method is easy to control since the elimination of hydrogen is suppressed. The organopolysiloxanes (Q) also do not have a tendency toward gelation. In addition, a high proportion of the chlorine in the starting materials is obtained as HCl gas.

The hydrolysable chlorine is present in the form of SiCl groups. In the first step, preferably at most 0.7 mol, more preferably 0.3 mol to 0.5 mol, and most preferably 0.4 mol to 0.5 mol of water is used per mol of hydrolysable chlorine.

The linear organopolysiloxanes (Q) having diorganosiloxy units and Si—H groups preferably have the general formula 1

in which
R is hydrogen or a $C_{1-18}$ hydrocarbon radical optionally substituted by halogen or cyano radicals,
$R^1$ is a $C_{1-18}$ hydrocarbon radical optionally substituted by halogen or cyano radicals,
m is an integer from 0 to 1000 and
n is an integer from 1 to 1000,
with the proviso that at least one radical R is hydrogen.

The diorganodichlorosilanes (A) used in the first step preferably have the general formula 2

in which $R^1$ has the above meaning. The monochlorosilanes (B) used in the first step preferably have the general formula 3

in which R has the above meaning. The dichlorosilanes (C) used in the first step preferably have the general formula 4

in which R has the above meaning. Preferably, the hydrocarbons R and $R^1$ are hydrocarbon radicals having 1 to 18 carbon atoms which are free from ethylenically or acetylenically unsaturated bonds.

Examples of hydrocarbon radicals R and $R^1$ are alkyl radicals such as the methyl, ethyl, n-propyl, isopropyl, n-butyl, isobutyl, tert-butyl, n-pentyl, isopentyl, neopentyl, and tert-pentyl radicals, hexyl radicals such as the n-hexyl radical, heptyl radicals such as the n-heptyl radical, octyl radicals such as the n-octyl radical and isooctyl radicals such as the 2,2,4-trimethylpentyl radical, nonyl radicals such as the n-nonyl radical, decyl radicals such as the n-decyl radical, dodecyl radicals such as the n-dodecyl radical, octadecyl radicals such as the n-octadecyl radical; cycloalkyl radicals such as the cyclopentyl, cyclohexyl, cycloheptyl and methylcyclohexyl radicals; aryl radicals such as the phenyl, naphthyl, anthryl and phenanthryl radicals; alkaryl radicals such as the o-, m-, and p-tolyl radicals, xylyl radicals and ethylphenyl radicals; and aralkyl radicals such as the benzyl radical, and the α- and the β-phenylethyl radicals.

Examples of substituted hydrocarbon radicals R and $R^1$ are cyanoalkyl radicals such as the β-cyanoethyl radical, and halogenated hydrocarbon radicals, for example haloalkyl radicals such as the 3,3,3-trifluoro-n-propyl radical, the 2,2,2,2',2',2'-hexafluoroisopropyl radical, the heptafluoroisopropyl radical, and haloaryl radicals, such as the o-, m-, and p-chlorophenyl radicals.

Preferably, the radicals R and $R^1$ are a phenyl radical or linear alkyl radical, in particular having 1 to 10, more particularly 1 to 6 carbon atoms. Particularly preferred hydrocarbon radicals R and $R^1$ are the n-propyl, ethyl and methyl radicals, in particular the methyl radical.

Preferably, m has a value of at most 200, more preferably at most 50. Preferably, n has a value of at most 500, more preferably at most 25.

Preferred mixtures used in the first step are (methyl=Me): $Me_3SiCl/Me_2SiHCl_2/MeSiHCl_2$ $Me_3SiCl/PropylMeSiCl_2/-MeSiHCl_2$, $Me_3SiCl/Me_2SiCl_2/PhenylMeSiCl_2/MeSiHCl_2$, Me$_2$SiHCl/Me$_2$SiCl$_2$, and Me$_2$SiHCl/Me$_2$SiCl$_2$/MeSiHCl$_2$. Particular preference is given to: Me$_3$SiCl/Me$_2$SiCl$_2$/MeSiHCl$_2$.

The method according to the invention is exceptionally suitable for producing sparingly volatile organopolysiloxanes (Q), e.g. polydimethylsiloxanes with Me$_2$HSi end groups or SiH-containing polysiloxanes with trimethylsilyl end groups. Preferably, the organopolysiloxanes (Q) have a viscosity of from 1 to 1200 mPas at 25° C.

In the hydrosilylation method according to the invention, compounds (F) containing carbon-carbon double bonds and/or carbon-carbon triple bonds are hydrosilylated with linear organopolysiloxanes (Q) having diorganosiloxy units and Si—H groups. The compound (F) may be silicon-free organic compounds with aliphatically unsaturated groups, or organosilicon compounds with aliphatically unsaturated groups.

Examples of organic compounds which can be used as component (F) are all types of olefins, such as 1-alkenes, 1-alkynes, vinylcyclohexane, 2,3-dimethyl-1,3-butadiene, 7-methyl-3-methylene-1,6-octadiene, 2-methyl-1,3-butadiene, 1,5-hexadiene, 1,7-octadiene, 4,7-methylene-4,7,8,9-tetrahydroindene, cyclopentene, methylcyclopentadiene, 5-vinyl-2-norbornene, bicyclo[2.2.1]hepta-2,5-diene, 1,3-diisopropenylbenzene, polybutadiene containing vinyl groups, 1,4-divinylcyclohexane, 1,3,5-triallylbenzene, 1,3,5-trivinylbenzene, 1,2,4-trivinylcyclohexane, 1,3,5-triisopropenylbenzene, 1,4-divinylbenzene, 3-methylheptadiene-(1,5), 3-phenylhexadiene-(1,5), 3-vinylhexadiene-(1,5) and 4,5-dimethyl-4,5-diethyloctadiene-(1,7), diallyl ether, diallylamine, diallyl carbonate, N,N'-diallylurea, triallylamine, tris(2-methylallyl)amine, 2,4,6-triallyloxy-1,3,5-triazine, triallyl-s-triazine-2,4,6(1H,3H,5H)-trione, diallyl malonate, allyl alcohols, allyl glycols, allyl glycidyl ether and allylsuccinic anhydride.

In principle, the method according to the invention is also suitable for the reaction of acrylates, such as, for example, N,N'-methylenebis(acrylamide), 1,1,1-tris(hydroxymethyl)propane triacrylate, 1,1,1-tris(hydroxymethyl)propane trimethacrylate, tripropylene glycol diacrylate, polyethylene glycol diacrylate, polyethylene glycol dimethacrylate or poly(propylene glycol)methacrylate. Furthermore, aliphatically unsaturated organosilicon compounds can be used as constituent (F).

If organosilicon compounds which have SiC-bonded radicals with aliphatic carbon-carbon multiple bonds are used as constituent (F), these are preferably those having units of the formula

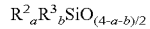
$$R^2_a R^3_b SiO_{(4-a-b)/2} \quad (I),$$

in which
R$^2$ are identical or different organic radicals free from aliphatic carbon-carbon multiple bonds,
R$^3$ are identical or different monovalent, optionally substituted, SiC-bonded hydrocarbon radicals with an aliphatic carbon-carbon multiple bond,
a is 0, 1, 2 or 3 and
b is 0, 1 or 2
with the proviso that the sum a+b is ≤4.

The organosilicon compounds (F) used according to the invention may either be silanes, i.e. compounds of the formula (I) where a+b=4, or siloxanes, i.e. compounds containing units of the formula (I) where a+b≤3.

Radical R$^2$ includes the monovalent radicals —F, —Cl, —Br, —CN, —SCN, —NCO, alkoxy radicals and SiC-bonded, optionally substituted hydrocarbon radicals which may be interrupted by oxygen atoms or the group —C(O)—.

Examples of radicals R$^2$ are alkyl radicals such as, for example, the methyl, ethyl, n-propyl, isopropyl, n-butyl, isobutyl, tert-butyl, n-pentyl, isopentyl, neopentyl, and tert-pentyl radicals, hexyl radicals such as the n-hexyl radical, heptyl radicals such as the n-heptyl radical, octyl radicals such as the n-octyl radical and the isooctyl radicals such as the 2,2,4-trimethylpentyl radical, nonyl radicals such as the n-nonyl radicals, decyl radicals such as the n-decyl radical, dodecyl radicals such as the n-dodecyl radical, and octadecyl radicals such as the n-octadecyl radical, cycloalkyl radicals such as the cyclopentyl, cyclohexyl, cycloheptyl and methylcyclohexyl radicals, aryl radicals such as the phenyl, naphthyl, anthryl and phenanthryl radicals, alkaryl radicals such as the o-, m-, and p-tolyl radicals, xylyl radicals and ethylphenyl radicals, and aralkyl radicals such as the benzyl radical and the α- and the β-phenylethyl radicals.

Examples of substituted radicals R$^2$ are haloalkyl radicals, such as the 3,3,3-trifluoro-n-propyl radical, the 2,2,2',2',2'-hexafluoroisopropyl radical and the heptafluoroisopropyl radical, and also haloaryl radicals, such as the o-, m- and p-chlorophenyl radicals.

Radical R$^2$ is preferably a monovalent SiC-bonded, optionally substituted hydrocarbon radical having 1 to 18 carbon atoms which is free from aliphatic carbon-carbon multiple bonds, more preferably a monovalent, SiC-bonded hydrocarbon radical having 1 to 6 carbon atoms which is free from aliphatic carbon-carbon multiple bonds, and in particular the methyl radical or phenyl radical.

Radical R$^3$ may be any desired groups accessible to an addition reaction (hydrosilylation) with an SiH-functional compound. If radical R$^3$ is an SiC-bonded, substituted hydrocarbon radical, the substituents are preferably halogen atoms, cyano radicals, alkoxy groups and siloxy groups. Radicals R$^3$ are preferably alkenyl and alkynyl groups having 2 to 16 carbon atoms, such as vinyl, allyl, methallyl, 1-propenyl, 5-hexenyl, ethynyl, butadienyl, hexadienyl, cyclopentenyl, cyclopentadienyl, cyclohexenyl, vinylcyclohexylethyl, divinylcyclohexylethyl, norbornenyl, vinylphenyl and styryl radicals, where vinyl, allyl and hexenyl radicals are particularly preferably preferred.

Preferred as component (F) are all terminal olefins and all allyl-containing, vinyl-containing and alkyne-containing systems, with allyl-containing systems being particularly preferred.

As organosilicon compound (Q), the linear organopolysiloxanes (Q) having diorganosiloxy units and Si—H groups described above are used. The organosilicon compound (Q) preferably contains Si-bonded hydrogen in the range from 0.02 to 1.7 percent by weight, based on the total weight of the organosilicon compound (Q).

The molecular weight of constituent (Q) in the case of siloxanes can vary within wide limits, for example between 10$^2$ and 10$^6$ g/mol. Thus, constituent (Q) may, for example, be a relatively low molecular weight SiH-functional oligosiloxane, or a highly polymeric polydimethylsiloxane having chain-position or terminal SiH groups, or a silicone resin having SiH groups. The structure of the molecules forming the constituent (Q) is not fixed either; in particular, the structure of a relatively high molecular weight, thus oligomeric or polymeric, SiH-containing siloxane may be linear, cyclic, branched or else resin-like, network-like.

In the method according to the invention, constituent (Q) is preferably used in an amount such that the molar ratio of aliphatically unsaturated groups of constituent (F) to SiH groups of constituent (Q) is between 0.1 and 20 and in the case of siloxanes, preferably between 1.0 and 5.0.

In the method according to the invention, as component (G) it is possible to use all catalysts which are useful for the addition of Si-bonded hydrogen onto aliphatically unsaturated compounds. Examples of such catalysts are compounds or complexes of precious metals comprising platinum, ruthenium, iridium, rhodium and palladium, such as, for example, platinum halides, platinum-olefin complexes, platinum-alcohol complexes, platinum-alcoholate complexes, platinum-ether complexes, platinum-aldehyde complexes, platinum-ketone complexes, including reaction products of $H_2PtCl_6.6H_2O$ and cyclohexanone, platinum-vinylsiloxane complexes, in particular platinum-divinyltetramethyldisiloxane complexes with or without a content of detectable inorganically bonded halogen, bis(γ-picolin)-platinum dichloride, trimethylenedipyridine-platinum dichloride, dicyclopentadiene-platinum dichloride, dimethylsulfoxide ethylene-platinum(II) dichloride and also reaction products of platinum tetrachloride with olefin and primary amine or secondary amine or primary and secondary amine, such as, for example, the reaction product of platinum tetrachloride dissolved in 1-octene with sec-butylamine. In a furthermore preferred embodiment of the method according to the invention, complexes of iridium with cyclooctadienes, such as, for example, μ-dichlorobis(cyclooctadiene)-diiridium(I), are used.

Preferably, the catalysts (G) are compounds or complexes of platinum, preferably platinum chlorides and platinum complexes, in particular platinum-olefin complexes and most preferably platinum-divinyltetramethyldisiloxane complexes. Catalyst (G) is preferably used in amounts of from 1 to 50 ppm by weight, calculated as elemental precious metal and based on the total weight of component (F) and (Q) present in the composition. Preference is given to using 2 to 10 ppm by weight.

Particular preference is given to using complexes which are soluble in glycols and/or polyols, particular preference being given to platinum complexes such as $H_2PtCl_6$ and $PtCl_4$. The catalyst is preferably present in the glycol and/or polyol in amounts of from 0.1 to 50% by weight, more preferably in amounts of from 0.5 to 20% by weight and most preferably in amounts of from 1% to 5% by weight. By means of filtering, the platinum compound precipitated out during the reaction can be recovered and treated.

The method according to the invention can be carried out in the presence or absence of organic solvent(s) (H). Examples of organic solvents (H) are all solvents which have also hitherto been able to be used in hydrosilylation reactions, such as toluene, xylene, isopropanol, acetone, isophorone and glycols. If organic solvents (H) are used, these are preferably toluene, isopropanol and glycols, and most preferably toluene. When organic solvents (H) are used, the amounts are preferably 5 to 60% by weight, more preferably 5 to 40% by weight, in each case based on the total weight of the reaction mixture.

In the method according to the invention, it is also possible to use all further substances (I) which are useful in hydrosilylation reactions. Preferably, no further substances are used in addition to components (Q), (F) to (I). The components (Q) and (F) to (I) used according to the invention may in each case be a single type of such a component, or else a mixture of at least two different types of such a component. All of the above symbols in the above formulae have their meanings in each case irrespective of one another. In all formulae, the silicon atom is tetravalent.

In the method of the invention, the components can be mixed together by any desired and known method. Preferably, in the method according to the invention, either all of the reagents apart from catalyst (G) are initially introduced and then the reaction is started by adding the catalyst, or all of the reagents apart from the Si—H-containing compounds (Q) are initially introduced and the Si H-containing compounds are then metered in.

The method according to the invention can be carried out continuously or discontinuously.

In the method according to the invention, the addition reaction of Si-bonded hydrogen onto aliphatic multiple bond can take place under the same conditions as in the hydrosilylation reactions known hitherto. Preferably, these are temperatures of from 20 to 200° C., more preferably from 60 to 140° C., and a pressure from 1 to 20 bar. However, it is also possible to use higher or lower temperatures and pressures.

The organosilicon compounds produced in the method of the invention can be used for all purposes for which modified organosilicon compounds are useful. The inventive method has the advantage that a considerable catalyst reduction can be achieved since the catalytic activity of the original catalyst can be considerably increased and prolonged. Furthermore, the method has the advantage that the color quality is improved (lower Hazen color number) and a lower fraction of toxic heavy metals in the hydrosilylation product, especially in the case of polysiloxanes, is achieved. Further advantages are shorter reaction times and/or lower reaction temperatures.

Unless stated otherwise, within the context of the present invention, all amount and percentage data are based on weight, all temperatures are 20° C. and all pressures are 1.013 bar (abs.). All viscosities are determined at 25° C.

In order to demonstrate the advantage of the novel method, the examples describe hydrosilylations with polyhydrogensiloxanes Q produced via a conventional equilibration method (example 1 and example 3) and via cohydrolysis methods (example 2 and example 4).

Comparative Examples not According to the Invention

Polyhydrogensiloxane Q1 is produced by equilibration of trimethylsilyl-terminated polymethylhydrogensiloxane and trimethylsilyl-terminated polydimethylsiloxane under acidic catalysis conditions with phosphonitrile chloride, analogous to the method described in EP 797612, example 5.

Examples According to the Invention

Polyhydrogensiloxane Q2 is produced as follows.

In a loop reactor (1), 92 kg/h of methyldichlorosilane, 98 kg/h of dimethyldichlorosilane and 5.0 kg/h of trimethylchlorosilane are fed in via line (5), 60 l/h of distillate from the thin-film evaporator (4) (comprises 30% by weight of low molecular weight hydrogenmethylsiloxanes and 70% by weight of toluene) are fed in via line (12) and hydrochloric acid from separator (3) is fed in via line (10) at 30° C. The hydrogen chloride produced is stripped off from the reactor in gaseous form. The partial hydrolysate emerging from the loop reactor (1) is fed as a homogenous phase via line (7) to the loop reactor (2), where it is mixed with 29 kg/h of water.

The reaction mixture emerging from the loop reactor (2) is fed via line (9) into the separator (3). There, it is separated into the upper, organic hydrolysate phase and the lower aqueous phase, which corresponds to a ca. 6% strength by weight hydrochloric acid. The lower phase is returned to the loop reactor (1) via line (10). The organic hydrolysate phase is heated over two distillation stages in the plant (4) at up to 160° C. and 1 mbar (absolute). The distillate stream (15) produced in the second distillation stage (14) is fed in its entirety to a rearrangement reactor (16), which is configured as a fluidized-bed reactor with bottom inflow and a catalyst bed of a sulfonated polystyrene resin. The rearrangement reaction is carried out at 20° C. and an absolute pressure of 1100 hPa.

The equilibrated rearranged DSV condensate (17) is fed back into the distillation part of the plant (4) again. The discharge (18) comprises linear trimethylsilyl-terminated hydrogenmethylpolysiloxane with dimethylsilyl groups Q2.

Q1 and Q2 each have a viscosity of 60 mPas and a hydrogen content of 0.73% by weight and correspond to the average formula $Me_3SiO(SiHMeO)_{29}(SiMe_2O)_{29}SiMe_3$.

Example 1

Not According to the Invention 134 g of polyhydrogensiloxane Q1 and 0.135 ml of the platinum catalyst solution G1 (1% strength solution of hexachloroplatinic acid in isopropanol) were initially introduced into a three-neck flask and heated to 105° C. 134 g of 1-octene were metered in continuously such that during the exothermic reaction a reaction temperature of 140° C. was not exceeded. The metering time was 40 minutes. The reaction mixture was stirred for a further two hours at 140° C. and then cooled to room temperature. The hydrogen number was determined as a measure of the reaction progress. The hydrogen number was 31 (desired value<10).

Example 2

According to the Invention

The previous example was repeated using the polyhydrogensiloxane Q2 prepared via cohydrolysis methods instead of Q1. The hydrogen number was 8.2 (desired: <10). After distilling off the volatile constituents at 140° C./vacuum<1 mbar and filtration, a pale beige alkyl-functional silicone oil was obtained with the following properties: Hazen color number (DIN ISO 6271): 85; viscosity 1110 mPas.

Example 3

Not According to the Invention

Example 1 was repeated using 0.215 ml of the platinum catalyst solution G2 (3% strength solution of hexachloroplatinic acid in 1,2-propanediol) instead of G1. Only a slightly exothermic reaction was observed. The hydrogen number was 183 (desired value<10).

Example 4

According to the Invention

The previous example was repeated using the polyhydrogensiloxane Q2 prepared by cohydrolysis methods instead of Q1. A strongly exothermic reaction was observed. The hydrogen number was 7.8 (desired: <10). After distilling off the volatile constituents at 140° C./vacuum<1 mbar and filtering off the precipitated-out platinum compound, a colorless alkyl-functional silicone oil was obtained with the following properties: Hazen color number (DIN ISO 6271): 8; viscosity 1296 mPas.

TABLE 1

|  | Polyhydrogensiloxane | Platinum catalyst solution | Hydrogen number |
|---|---|---|---|
| Example 1 (not acc. to the inv.) | Q1 | G1 | 31 |
| Example 2 | Q2 | G1 | 8.1 |
| Example 3 (not acc. to the inv.) | Q1 | G2 | 183 |
| Example 4 | Q2 | G2 | 7.8 |

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A method for the hydrosilylation of compound(s) containing carbon-carbon double bonds and/or carbon-carbon triple bonds with linear organopolysiloxanes having diorganosiloxy units and Si—H groups, comprising hydrosilylating the compound(s) containing carbon-carbon double bonds and/or carbon-carbon triple bonds with a linear organopolysiloxane comprising diorganosiloxy units and Si—H groups, wherein the linear organopolysiloxane comprising diorganosiloxy groups and SiH groups is produced by a) reacting at least one diorganodichlorosilane and at least one monochlorosilane and optionally one or more dichlorosilanes with water in a first step, where at least one of the monochlorosilane or dichlorosilane contains Si—H groups to give a partial hydrolysate and gaseous hydrogen chloride and, b) in a second step, treating the partial hydrolysate with water in order to remove further SiCl groups still present to form hydrochloric acid, producing a hydrolysate containing the linear organopolysiloxane comprising diorganosiloxy groups and Si—H groups.

2. The method of claim 1, wherein at most 0.7 mol of water is used per mole of hydrolyzable chlorine in the first step.

3. The method of claim 1, wherein the hydrosilylation is carried out using at least one compound or complex of platinum as a catalyst.

* * * * *